United States Patent [19]

Ishikawa et al.

[11] Patent Number: 5,824,778
[45] Date of Patent: Oct. 20, 1998

[54] CHEMICALLY-MODIFIED G-CSF

[75] Inventors: Rika Ishikawa, Higashiyamato; Yuji Okada; Makoto Kakitani, both of Maebashi, all of Japan

[73] Assignee: Kirin-Amgen, Inc., Thousand Oaks, Calif.

[21] Appl. No.: 983,620

[22] Filed: Nov. 30, 1992

Related U.S. Application Data

[63] Continuation of Ser. No. 566,451, filed as PCT/JP89/01292 Dec. 22, 1989 published as WO90/06952, abandoned.

[30] Foreign Application Priority Data

| Dec. 22, 1988 | [JP] | Japan | 324747/88 |
| Jul. 31, 1989 | [JP] | Japan | 1-199176 |

[51] Int. Cl.$^6$ .................................................. C07K 14/53
[52] U.S. Cl. ..................... 530/351; 530/395; 530/402; 530/405; 930/145
[58] Field of Search .................................. 530/351, 395, 530/402, 405, 409, 410; 435/69.5, 69.6; 930/145; 525/54.1

[56] References Cited

U.S. PATENT DOCUMENTS

| 4,179,337 | 12/1979 | Davis et al. ............................. | 424/44 |
| 4,609,546 | 9/1986 | Hirantani ................................ | 530/399 |
| 4,766,106 | 8/1988 | Katre et al. ............................. | 514/2 |
| 4,791,192 | 12/1988 | Nakagawa et al. ..................... | 530/399 |
| 4,810,643 | 3/1989 | Souza ..................................... | 435/192.3 |
| 4,833,127 | 5/1989 | Ono et al. .............................. | 530/395 |
| 4,847,325 | 7/1989 | Shadle et al. .......................... | 530/351 |
| 4,894,226 | 1/1990 | Aldwin et al. ......................... | 424/85.2 |
| 4,904,584 | 2/1990 | Shaw ...................................... | 530/351 |
| 5,166,322 | 11/1992 | Shaw et al. ............................ | 530/351 |
| 5,194,592 | 3/1993 | Yoshida ................................. | 530/388.23 |

FOREIGN PATENT DOCUMENTS

| 0154316 | 9/1985 | European Pat. Off. . |
| 210761 | 2/1987 | European Pat. Off. . |
| 215126 | 3/1987 | European Pat. Off. . |
| 236987 | 9/1987 | European Pat. Off. . |
| 247860 | 12/1987 | European Pat. Off. . |
| 335423 | 10/1989 | European Pat. Off. . |
| 57-192435 | 11/1982 | Japan . |
| 6142558 | 9/1986 | Japan . |
| 62-115280 | 5/1987 | Japan . |
| 62-129298 | 6/1987 | Japan . |
| 62-236497 | 10/1987 | Japan . |
| 62-36488 | 10/1987 | Japan . |
| 62-289522 | 12/1987 | Japan . |
| 62-503171 | 12/1987 | Japan . |
| 6310800 | 1/1988 | Japan . |
| 500636 | 3/1988 | Japan . |
| 60938 | 3/1988 | Japan . |
| 126900 | 5/1988 | Japan . |
| 126677 | 5/1989 | Japan . |
| 00056 | 1/1987 | WIPO . |
| 9009798 | 9/1990 | WIPO . |
| 9012874 | 11/1990 | WIPO . |

OTHER PUBLICATIONS

Morstyn, *The Lancet* 26 Mar. 1988, 667–671.
Hershfield et al, The New England J. of Medicine 316(10): 589–596, 05 Mar. 1987.
Katre et al, *P.N.A.S.* 84:1487–1491, Mar.1987.

(List continued on next page.)

*Primary Examiner*—John Ulm
*Attorney, Agent, or Firm*—Marshall, O'Toole, Gerstein, Murray & Borun

[57] ABSTRACT

The present invention provides a chemically-modified protein prepared by binding polyethylene glycol to a polypeptide characterized by being the product of expression by a host cell of an exogenous DNA sequence and substantially having the following amino acid sequence:

(Met)$_n$

| Thr | Pro | Leu | Gly | Pro | Ala | Ser | Ser | Leu | Pro | Gln |
| Ser | Phe | Leu | Leu | Lys | Cys | Leu | Glu | Gln | Val | Arg |
| Lys | Ile | Gln | Gly | Asp | Gly | Ala | Ala | Leu | Gln | Glu |
| Lys | Leu | Cys | Ala | Thr | Tyr | Lys | Leu | Cys | His | Pro |
| Glu | Glu | Leu | Val | Leu | Leu | Gly | His | Ser | Leu | Gly |
| Ile | Pro | Trp | Ala | Pro | Leu | Ser | Ser | Cys | Pro | Ser |
| Gln | Ala | Leu | Gln | Leu | Ala | Gly | Cys | Leu | Ser | Gln |
| Leu | His | Ser | Gly | Leu | Phe | Leu | Tyr | Gln | Gly | Leu |
| Leu | Gln | Ala | Leu | Glu | Gly | Ile | Ser | Pro | Glu | Leu |
| Gly | Pro | Thr | Leu | Asp | Thr | Leu | Gln | Leu | Asp | Val |
| Ala | Asp | Phe | Ala | Thr | Thr | Ile | Trp | Gln | Gln | Met |
| Glu | Glu | Leu | Gly | Met | Ala | Pro | Ala | Leu | Gln | Pro |
| Thr | Gln | Gly | Ala | Met | Pro | Ala | Phe | Ala | Ser | Ala |
| Phe | Gln | Arg | Arg | Ala | Gly | Gly | Val | Leu | Val | Ala |
| Ser | His | Leu | Gln | Ser | Phe | Leu | Glu | Val | Ser | Tyr |
| Arg | Val | Leu | Arg | His | Leu | Ala | Gln | Pro | | |

(n = 0 or 1)

The chemically-modified protein according to the present invention has a much longer lasting neutrophil-increasing activity than that of the intact human G-CSF, enabling fewer numbers of administration with a lower dose.

2 Claims, 5 Drawing Sheets

OTHER PUBLICATIONS

Yamasaki et al *Chem Abst*112, 1990, #1398342.

Goodson et al., Bio/Technology, 8, pp. 343–346 (1990).

Habeeb et al., Anal. Biochem., 14, pp. 328–336 (1966).

Katre et al., Proc. Nat'l. Acad. Sci. USA, 84, pp. 1487–1491 (1987).

Kodera et al., Seikagaku, 60(9), 1005–1018 (1988) "Frontier of chemical modification of proteins: Application of polyethyleneglycol–modified enzymes in biotechnical processes".

Koerholz et al., Eur. J. Haematol., 42(5), pp. 417–424 (1982).

Laemmli, Nature, 227, pp. 680–685 (1970).

Ralph et al., Blood, 66, pp. 633–639 (1988).

Stocks et al., Anal. Biochem., 154, pp. 232–234 (1986).

Welte et al., Proc. Nat'l. Acad. Sci. (USA), 82, pp. 1526–1530 (1985).

CHEMICALLY-MODIFIED G-CSF

This is a Continuation of U.S. application Ser. No. 07/566,451, filed as PCT/JP89/01292 Dec. 22, 1989, published as WO90/06952, now abandoned.

TECHNICAL FIELD

The present invention relates to a chemical modification of granulocyte colony-stimulating factor (G-CSF), by which the chemical and/or physiological properties of G-CSF can be changed.

BACKGROUND ART

Human G-CSF is one of the haematopoietic growth factors. It has been shown to be present in the conditioned medium of a human bladder carcinoma cell line denominated 5637 (ATCC HT8-9) (Welte et al., Proc. Natl. Acad. Sci. (USA), 82, pp. 1526–1530, (1985)). The determination of a DNA sequence encoding human G-CSF (Japanese Patent Application Laying Open KOHYO No. 500636/88) has enabled the production of human G-CSF by means of recombinant genetic techniques.

Human G-CSF may be useful in the treatment of general haematopoietic disorders including those arising from chemotherapy or from radiation therapy. It may be also useful in bone marrow transplantation. Wound healing burn treatment and the treatment of bacterial inflammation may also benefit from the application of human G-CSF (Welte et al., supra.).

It is generally observed that physiologically-active proteins administered into a body can show their pharmacological activity only for a short period of time due to their high clearance rate in the body. Furthermore, high hydrophobicity of the proteins reduces their stability.

For the purpose of decreasing the clearance rate, improving stability or abolishing antigenicity of the proteins, some methods have been proposed wherein the proteins are chemically modified by using polyethylene glycol. Japanese Patent Application Laying Open KOHYO No. 289522/87, for EXAMPLE, discloses the reduction in immunogenicity of TNF which has been modified by polyethylene glycol. Japanese Patent Application Laying Open KOHYO No. 503171/87 discloses with respect to IL-2 and IFN-β the reduction in immunogenicity and aggregating tendencies in an aqueous solution, and the prolongation of half-life in blood. In addition, there are disclosed the prolongation of half-life in blood and the disappearance of antigenicity or immunogenicity owing to the modification by polyethylene glycol with respect to a plasminogen activator (Japanese Patent Application Laying Open KOHYO No.60938/88), IL-2, IFN-γ and SOD (Japanese Patent Application Laying Open KOHYO No.10800/88), and IAP (Japanese Patent Application Laying Open KOHYO No.126900/88).

However, these prior art publications have not disclosed an improvement in biological activity and pharmacokinetics, which may be expected as a result of the modification of human G-CSF by polyethylene glycol.

Accordingly, it has been desired to prolong the half-life of human G-CSF in the body so as to enhance its effects, as may be expected. Furthermore, a G-CSF product which can accelerate recovery from neutropenia has been desired.

DISCLOSURE OF INVENTION

After vigorous investigations in order to solve the above problems, the present inventors have now found that their solution can be realized by binding polyethylene glycol to human G-CSF, and have completed the present invention..

Any purified and isolated human G-CSF which is produced by host cells such as *E. coli* and animal cells transformed by using recombinant genetic techniques may be used in the present invention.

Among them, the human G-CSF which is produced by the transformed *E. coli* is particularly preferable. Such human G-CSF may be obtained in large quantities with high purity and homogeneity and substantially has the following amino acid sequence:

(Met)n

| Thr | Pro | Leu | Gly | Pro | Ala | Ser | Ser | Leu | Pro | Gln |
|---|---|---|---|---|---|---|---|---|---|---|
| Ser | Phe | Leu | Leu | Lys | Cys | Leu | Glu | Gln | Val | Arg |
| Lys | Ile | Gln | Gly | Asp | Gly | Ala | Ala | Leu | Gln | Glu |
| Lys | Leu | Cys | Ala | Thr | Tyr | Lys | Leu | Cys | His | Pro |
| Glu | Glu | Leu | Val | Leu | Leu | Gly | His | Ser | Leu | Gly |
| Ile | Pro | Trp | Ala | Pro | Leu | Ser | Ser | Cys | Pro | Ser |
| Gln | Ala | Leu | Gln | Leu | Ala | Gly | Cys | Leu | Ser | Gln |
| Leu | His | Ser | Gly | Leu | Phe | Leu | Tyr | Gln | Gly | Leu |
| Leu | Gln | Ala | Leu | Glu | Gly | Ile | Ser | Pro | Glu | Leu |
| Gly | Pro | Thr | Leu | Asp | Thr | Leu | Gln | Leu | Asp | Val |
| Ala | Asp | Phe | Ala | Thr | Thr | Ile | Trp | Gln | Gln | Met |
| Glu | Glu | Leu | Gly | Met | Ala | Pro | Ala | Leu | Gln | Pro |
| Thr | Gln | Gly | Ala | Met | Pro | Ala | Phe | Ala | Ser | Ala |
| Phe | Gln | Arg | Arg | Ala | Gly | Gly | Val | Leu | Val | Ala |
| Ser | His | Leu | Gln | Ser | Phe | Leu | Glu | Val | Ser | Tyr |
| Arg | Val | Leu | Arg | His | Leu | Ala | Gln | Pro | | |

(n = 0 or 1)

The above human G-CSF may, for example, be prepared according to a method disclosed in Japanese Patent Application Laying Open KOHYO No.500636/88. The term "substantially has the following amino acid sequence" means that the above amino acid sequence may include one or more amino-acid changes (deletion, addition, insertion or replacement) as long as such changes will not cause any disadvantageous non-similarity in function to a naturally-occurring human G-CSF.

It is more preferable to use the human G-CSF substantially having the above amino acid sequence, in which at least one lysine, aspartic acid or glutamic acid. residue is included.

According to the present invention, polyethylene glycol is covalently bound through amino acid residues of the polypeptide of human G-CSF. The amino acid residue may be any reactive one having, for example, free amino or carboxyl groups, to which a terminal reactive group of an activated polyethylene glycol may be bound. The amino acid residues having the free amino groups may include lysine residues and N-terminal amino acid residue, and those having the free carboxyl group may include aspartic acid, glutamic acid residues and C-terminal amino acid residue.

A molecular weight of the polyethylene glycol used in the present invention is not restricted to any particular range, being, however, normally of from 500–20,000 and preferably of from 4,000–10,000.

Polyethylene glycol is bound onto human G-CSF via a terminal reactive group (or "a spacer"). Polyethylene glycol having the spacer is hereinafter referred to as "an activated polyethylene glycol". The spacer, for example, is a terminal reactive group which mediates a bond between the free amino or carboxyl groups and polyethylene glycol. The activated polyethylene glycol which may be bound to the free amino group includes N-hydroxysuccinylimide polyethylene glycol having the following formula:

which may be prepared by activating succinic acid ester of polyethylene glycol with N-hydroxysuccinylimide. Another activated polyethylene glycol which may be bound to free amino group is 2,4-bis(O-methoxypolyethyleneglycol)-6-chloro-s-triazine having the following formula:

which had been prepared by reacting polyethylene glycol monomethyl ether with cyanuric chloride. The activated polyethylene glycol which is bound to the free carboxyl group includes polyoxyethylenediamine having the following formula:

The chemical modification through a covalent bond may be performed under any suitable condition generally adopted in a reaction of a biologically active substance with the activated polyethylene glycol. In case where the reactive amino acid residues in human G-CSF have free amino groups, the above modification is preferably carried out in a buffer solution such as phosphate and borate (pH 7.5–10.0) for 1–5 hrs at 4°–37° C. The activated polyethylene glycol may be used in 1–200 times, preferably 5–50 times the molar amount of the number of free amino groups of human G-CSF. On the other hand, where the reactive amino acid residues in human G-CSF have the free carboxyl groups, the above modification is preferably carried out in pH 3.5–5.5, for example, the modification with polyoxyethylenediamine is carried out at the presence of carbodiimide (pH 4.0–5.0) for 1–24 hrs at 4°–37° C. The activated polyethylene glycol may be used in 1–200 times the molar amount of the number of free carboxyl groups of human G-CSF.

The extent of the modification of the amino acid residues may be optionally controlled depending on an amount of the activated polyethylene glycol used in the modification.

A polyethylene glycol-modified human G-CSF, namely chemically modified protein according to the present invention, may be purified from a reaction mixture by conventional methods which are used for purification of proteins, such as dialysis, salting-out, ultrafiltration, ion-exchange chromatography, gel chromatography and electrophoresis. Ion-exchange chromatography is particularly effective in removing unreacted polyethylene glycol and human G-CSF.

The present polyethylene glycol-modified human G-CSF has a more enduring pharmacological effect, which may be possibly attributed to its prolonged half-life in body.

Furthermore, it is observed that the present polyethylene glycol-modified human G-CSF may accelerate recovery from neutropenia.

The present polyethylene glycol-modified human G-CSF has essentially the same biological activity as an intact human G-CSF and may accordingly be used in the same application as that. The polyethylene glycol-modified human G-CSF has an activity for increasing the number of neutrophils, and it is therefore useful in the treatment of general haematopoietic disorders including those arising from chemotherapy or from radiation therapy. It may be also useful in the treatment of infection and under receiving the therapy of bone marrow transplantation.

The present polyethylene glycol-modified human G-CSF may be formulated into pharmaceuticals containing also a pharmaceutically acceptable diluent, an agent for preparing an isotonic solution, a pH-conditioner and the like in order to administer them into a patient.

The above pharmaceuticals may be administered subcutaneously, intramuscularly, intravenously or orally, depending on a purpose of treatment. A dose may be also based on the kind and condition of the disorder of a patient to be treated, being normally between 0.1 $\mu$g and 5 mg by injection and between 0.1 mg and 5 g in an oral administration for an adult

BEST MODE FOR CARRYING OUT THE INVENTION

The present invention will be further illustrated by referring to the following EXAMPLEs which, however, are not be construed as limiting the scope of the present invention.

EXAMPLE 1

Preparation of PEG (4,500) G-CSF

Recombinant human G-CSF (Japanese Patent Application Laying Open KOHYO No. 500636/88) having the following amino acid sequence was used for the chemical modification according to the present invention:

```
                                                        Met
Thr Pro Leu Gly Pro Ala Ser Ser Leu Pro Gln
Ser Phe Leu Leu Lys Cys Leu Glu Gln Val Arg
Lys Ile Gln Gly Asp Gly Ala Ala Leu Gln Glu
Lys Leu Cys Ala Thr Tyr Lys Leu Cys His Pro
Glu Glu Leu Val Leu Leu Gly His Ser Leu Gly
Ile Pro Trp Ala Pro Leu Ser Ser Cys Pro Ser
Gln Ala Leu Gln Leu Ala Gly Cys Leu Ser Gln
Leu His Ser Gly Leu Phe Leu Tyr Gln Gly Leu
Leu Gln Ala Leu Glu Gly Ile Ser Pro Glu Leu
Gly Pro Thr Leu Asp Thr Leu Gln Leu Asp Val
Ala Asp Phe Ala Thr Thr Ile Trp Gln Gln Met
Glu Glu Leu Gly Met Ala Pro Ala Leu Gln Pro
Thr Gln Gly Ala Met Pro Ala Phe Ala Ser Ala
Phe Gln Arg Arg Ala Gly Gly Val Leu Val Ala
Ser His Leu Gln Ser Phe Leu Glu Val Ser Tyr
Arg Val Leu Arg His Leu Ala Gln Pro
```

The activated polyethylene glycol (PEG) used was Methoxypolyethyleneglycol-Succinimydyl Succinate (Nippon Oil and Fats, Co., Ltd.) which had been prepared by activating a succinic acid ester of polyethylene glycol with an average molecular weight of about 4,500 with N-hydroxysuccinylimide.

The human G-CSF was incubated in 0.25M sodium borate buffer (pH 8.0) for 1 hr at 4° C. with the activated PEG in 1–50 times the molar amount of the number of the free amino groups in the human G-CSF. The resulting product was applied to Sephadex G25 which had been equilibrated with 10 mM $NH_4HCO_3$ for buffer-exchange, and then to DEAE ion-exchange chromatography so as to separate the PEG-modified human G-CSF from the agent and, if necessary, an unreacted human G-CSF. The resultant PEG-modified human G-CSF is hereinafter referred to as "PEG (4,500) G-CSF".

EXAMPLE 2

Characterization of PEG (4,500) G-CSF

PEG (4,500) G-CSF prepared in EXAMPLE 1 was characterized by the number of unmodified amino groups and a molecular weight estimated by SDS-PAGE.

The number of the unmodified amino groups was determined by reacting them with 0.1% TNBS in 4% $NaHCO_3$ followed by measurement of absorbance at 335 nm (Habeeb et al., Anal. Biochem., 14, pp.328–336, (1966)).

The molecular weight of PEG (4,500) G-CSF was determined by SDS-PAGE (16% gel, CBB staining) according to a method of Laemli, Nature, 227, p.680, 1970. Each lane on the gel was scanned by using a chromato-scanner (SHIMADZU CORPORATION: CS-930) after staining.

Figure 1:
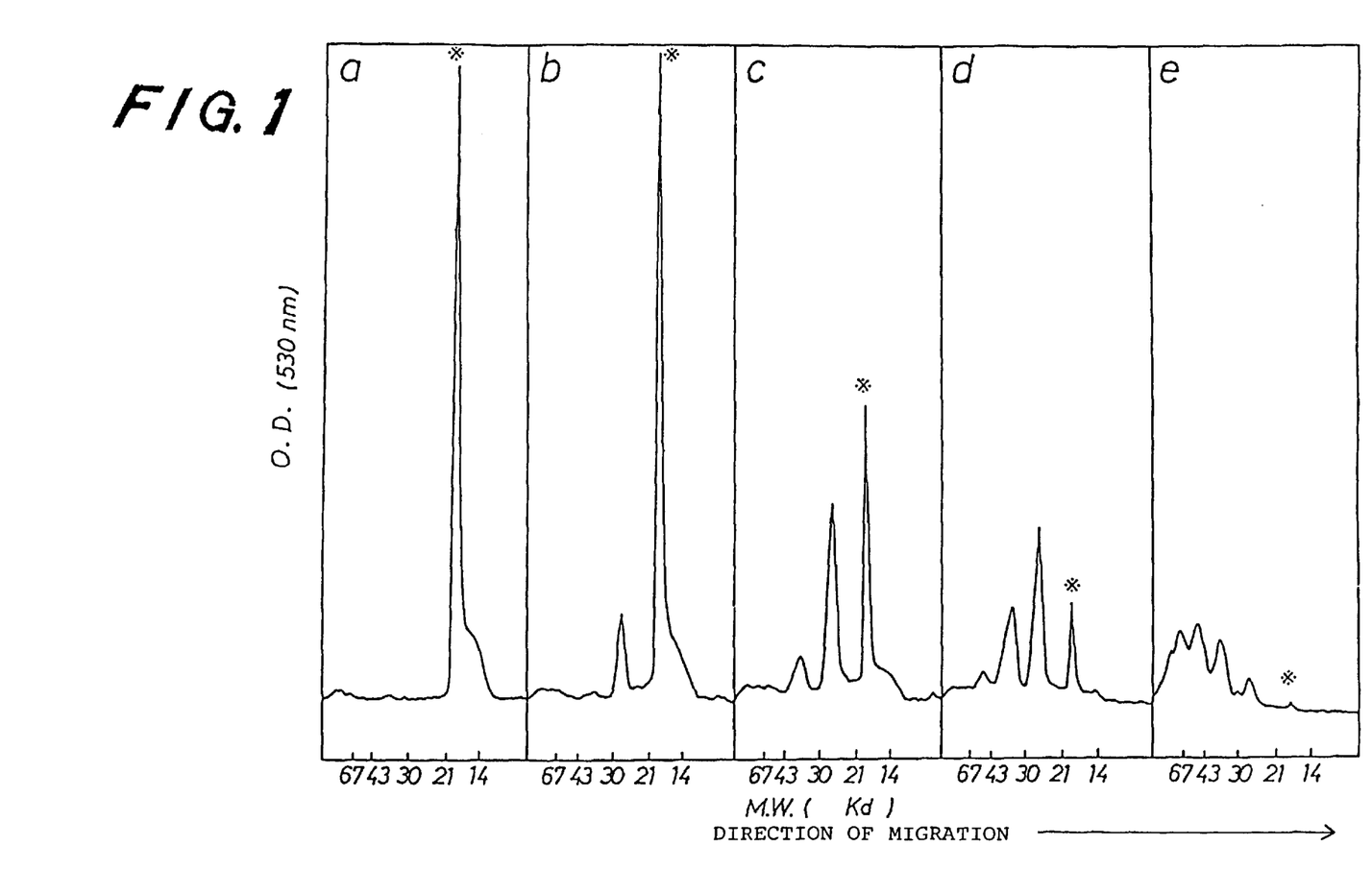
FIG. 1 shows scanning patterns of PEG (4,500) G-CSF obtained by SDS-PAGE. The molar ratio of the activated PEG to the free amino groups of the human G-CSF is 0 for (a), 1 for (b), 5 for (c), 10 for (d) and 50 for (e), respectively. The peak of the intact human G-CSF is marked of *.

When a molar ratio of the activated PEG to the number of free amino groups of human G-CSF increased, the extent of the modification also increased. The product prepared in said molar ratio of 1 has in addition to a band corresponding to an intact human G-CSF (19K) another band with an apparent molecular weight of about 26K (FIG. 1). With respect to the product prepared in the molar ratio of 5 or more, a band with a higher molecular weight was observed besides the above two bands. By scanning the resulting gel, a content of each band was determined. From the result in TABLE 1, it is estimated that the band of 26K consists of human G-CSF wherein one human G-CSF molecule is bound with one activated PEG molecule and that a band of 34K consists of human G-SCF wherein one human G-CSF molecule is bound with two activated PEG molecules.

TABLE 1

Characterization of PEG (4,500) G-CSF

| | Distribution | | | Modified $NH_2$ | Unmodified $NH_2$ |
|---|---|---|---|---|---|
| PEG/$NH_2$ | 19K | 26K | 34K | (%) | (an average number) |
| 1 | 86 | 12 | | 5 | 4.8 |
| 2 | 68 | 31 | 1 | 15 | 4.3 |
| 3 | 56 | 42 | 2 | 15 | 4.3 |
| 4 | 36 | 48 | 16 | 20 | 4.0 |
| 5 | 31 | 49 | 20 | 27 | 3.7 |
| 6 | 25 | 50 | 25 | 27 | 3.7 |
| 7 | 20 | 50 | 28 | 27 | 3.7 |

It was found that based on patterns obtained by SDS-PAGE of the fractions from the ion-exchange chromatography (shown in FIG. 1) that the human G-CSF with a higher modification extent was eluted faster from a column and that the fraction finally eluted therefrom contained the intact human G-CSF.

The scanning patterns by SDS-PAGE of PEG (4,500) G-CSFs including those obtained with a higher molar ratio of PEG/$NH_2$ are shown in FIG. 1.

EXAMPLE 3

Preparation of PEG (10,000) G-CSF

The same human G-CSF as used in EXAMPLE 1 was modified by an activated polyethylene glycol (an activated PEG 2; Seikagaku Kogyo K.K.) with a molecular weight of about 10,000 having the following formula:

which had been prepared by reacting polyethylene glycol monomethyl ether with cyanuric chloride.

The human G-CSF was incubated with the activated PEG 2 at 5 times the molar amount of free amino groups of the human G-CSF in 0.25M sodium borate buffer solution (pH 10.0) for 1 hr at room temperature. The resulting product was applied to Sephadex G25 which had been equilibrated with 10 mM $NH_4HCO_3$ for buffer-exchange, and then to DEAE ion-exchange chromatography to separate the PEG-modified human G-CSF from an unreacted human G-CSF and reagent. The estimation of a molecular weight of the product by SDS-PAGE as in EXAMPLE 2 has revealed that its average molecular weight is about 45K with distributed among 30K (10%), 40K (70%) and 66K (20%). The resultant PEG-modified human G-CSF is hereinafter referred to as "PEG (10,000) G-CSF".

Moreover, human G-CSF was incubated with the activated PEG 2 at 10 times the molar amount of free amino groups of the human G-CSF in 0.25M sodium borate buffer solution (pH 10.0) for 2 hrs at room temperature. The resulting product was subjected to separation in the same manner as stated above.

It is estimated in the same manner as in EXAMPLE 2 that the product of 30K consists of human G-CSF wherein one human G-CSF molecule is coupled with one activated PEG molecule.

Furthermore, the human G-CSF was incubated with the activated PEG 2 at 50 times the molar amount of free amino groups of the human G-CSF.

The estimation of a molecular weight of the resulting products by SDS-PAGE as in EXAMPLE 2 has revealed that its average molecular weight is about 51K with distributed among 40K (58 %) and 66K (42%).

EXAMPLE 4

Preparation of PEG (4,000) G-CSF

PEG-modified human G-CSF was prepared by covalently binding an activated polyethylene glycol, or polyoxyethylenediamine with an average molecular weight of 4,000 (Nippon Oil and Fats Co., Ltd.) to the above human G-CSF through the free carboxyl group thereof.

The human G-CSF and the activated polyethylene glycol at 60 times the molar amount of the free carboxyl groups of the human G-CSF were incubated in the presence of 0.05M 1-ethyl-3-(3-dimethylaminopropyl)carbodiimide at a room temperature for overnight. The reaction was terminated by adding 1M sodium acetate (pH 4.75) and further incubated at 25° C. in the presence of 0.5M hydroxyamine for 5 hrs in order to regenerate tyrosine residues. The resulting product was subjected to gel chromatography on TSK G3000SW which had been equilibrated with 10 mM sodium acetate (pH 5.5) to separate the PEG-modified human G-CSF from an unreacted human G-CSF and reagent. The estimation of a molecular weight of the product by SDS-PAGE as in EXAMPLE 2 has revealed that its molecular weight is distributed among 27K (70%), 35K (20%) and 42K (10%). The resultant PEG-modified human G-CSF is hereinafter referred to as "PEG (4,000) G-CSF".

EXAMPLE 5

In Vivo Biological Assay of PEG (4,500) G-CSF

Male ICR mice (Experiment I: 4 weeks old, Experiment II: 8 weeks old) were used for in vivo assays for pharmacological activity of PEG (4,500) G-CSF obtained in EXAMPLE 1. Samples of the intact human G-CSF and PEG (4,500) G-CSF were intravenously injected into mice at a dose of 10 µg or 100 µg protein/kg. At 24 hrs (10 µg protein/kg) or 32 hrs (100 µg protein/kg) after the injection, blood was collected from orbital vein and leukocytes were counted by an automated blood cell counter E-2000 (Toa Medical Electronics, Japan). At the same time, a blood smear was subjected to Wright-Giemsa stain and the leukocyte fraction was determined by an automated blood cell analyzer MICROX (OMRON TATEISI ELECTRONICS CO.) to count the number of neutrophils. The results are summarized in TABLE 2 below.

In TABLE 2, PEG (4,500) G-CSF (1) is a product obtained in the reaction wherein the molar ratio of the activated PEG/the free amino group was five (FIG. 1, C), PEG (4,500) G-CSF (2) is a 26K fraction obtained from DEAE ion-exchange chromatography, and PEG (4,500) G-CSF (3) is a high molecular fraction (26K:14%, 34K:55%, >34K:28%) obtained from said DEAE ion-exchange chromatography.

From the above results, it is observed that the increase in the number of neutrophils in the mice injected with PEG (4,500) G-CSFs (1), (2) and (3) was much larger than the increase in the number of neutrophils in the mice injected with the intact G-CSF. Especially, PEG (4,500) G-CSFs (1) and (3) with a higher extent of the modification showed a remarkable increase in the number of neutrophils.

When human G-CSF is injected into mice at a dose of 10 µg protein/kg, the number of neutrophils increases, and generally at 6–12 hrs after the injection, it reaches maximum. After that, the number of neutrophils decreases slowly to a basal level about 30 hrs after injection. The number of neutrophils decreases to almost a basal level after 24 hrs. Based on the foregoing time periods, it was determined that in the case of 100 µg protein/kg injections, the time for collection of blood was 32 hrs after injection. Accordingly, the above result that the numbers of neutrophils in the mice injected with PEG (4,500) G-CSFs (1), (2) and (3) are higher than those in the mice injected with the intact hG-CSF may indicate that the activity of human G-CSF in mice has been extended by the present modification.

An unreacted mixture of human G-CSF and PEG only showed the same result as the intact human G-CSF (Data are not shown).

TABLE 2

Pharmacological activity (in vivo) of PEG-modified human G-CSF

| Group | | N | neutrophils (× $10^2/\mu l$) | Ratio (to vehicle) |
|---|---|---|---|---|
| a. 10 µg/kg | | | | |
| <Exp. I> | | | | |
| vehicle | | 5 | 5.6 ± 1.0 | 1.0 |
| control | G-CSF | 6 | 9.6 ± 1.4 | 1.7 |
| PEG(4500) | G-CSF(1) | 6 | 20.8 ± 2.6 | 3.7 |
| PEG(4500) | G-CSF(2) | 6 | 17.5 ± 3.0 | 3.1 |
| <Exp. II> | | | | |
| vehicle | | 6 | 12.3 ± 1.7 | 1.0 |
| control | G-CSF | 6 | 27.1 ± 4.6 | 2.2 |
| PEG(4500) | G-CSF(3) | 6 | 54.0 ± 7.2 | 4.4 |
| b. 100 µg/kg | | | | |
| <Exp. I> | | | | |
| vehicle | | 6 | 6.6 ± 0.7 | 1.0 |
| control | C-CSF | 6 | 18.5 ± 2.3 | 2.8 |
| PEG(4500) | G-CSF(1) | 6 | 42.9 ± 4.3 | 6.5 |
| PEG(4500) | G-CSF(2) | 6 | 22.6 ± 1.9 | 3.4 |

EXAMPLE 6

In Vivo Biological Assay of PEG (4,000) G-CSF

Male ICR mice (7 weeks old) were used for in vivo assays for pharmacological activity of PEG (4,000) G-CSF obtained in EXAMPLE 4. Samples of the intact human G-CSF and PEG (4,000) G-CSF were intravenously injected into mice at a dose of 10 μg protein/kg. At 24 hrs after the injection, blood was collected from the orbital vein and the number of neutrophils was counted as in EXAMPLE 5. The results are shown in TABLE 3.

It has been determined that PEG (4,000) G-CSF in which the activated PEG is bound through the free carboxyl group also increased the number of neutrophils more than intact human G-CSF.

TABLE 3

Pharmacological activity (in vivo) of PEG (4,000) G-CSF

| Group | Number of Animals | Number of Neutrophils ($\times 10^2/\mu l$) | Ratio (to vehicle) |
|---|---|---|---|
| Vehicle | 6 | 10.9 + 1.0 | 1.0 |
| G-CSF (control) | 6 | 16.4 + 1.4 | 1.5 |
| PEG (4,000) G-CSF | 6 | 23.3 + 2.5 | 2.1 |

EXAMPLE 7

Effects of PEG-Modified Human G-CSFs on Increasing Mice Neutrophils

Male ICR mice (7 weeks old) were used for in vivo assays for pharmacological activity of PEG (4,500) G-CSF and PEG (10,000) G-CSF obtained in EXAMPLEs 1 and 3, respectively. The PEG (4,500) G-CSF used is a high molecular fraction from DEAE ion-exchange chromatography of a product obtained in the reaction wherein the molar ratio of the activated PEG/the free amino group was fifty (an average molecular weight of 60K; 38K:20%, 58K:54%, 80K:27%). Samples of the human G-CSF, PEG (4,500) G-CSF and PEG (10,000) G-CSF were intravenously injected into mice at a dose of 10 μg protein/kg. At 6, 24, 32, 48 and 72 hrs after the injection, blood was collected from orbital vein and the number of neutrophils was counted as in EXAMPLE 5, except for using an automated blood cell counter CC180-A (Toa Medical Electronics, Japan).

Figure 2:
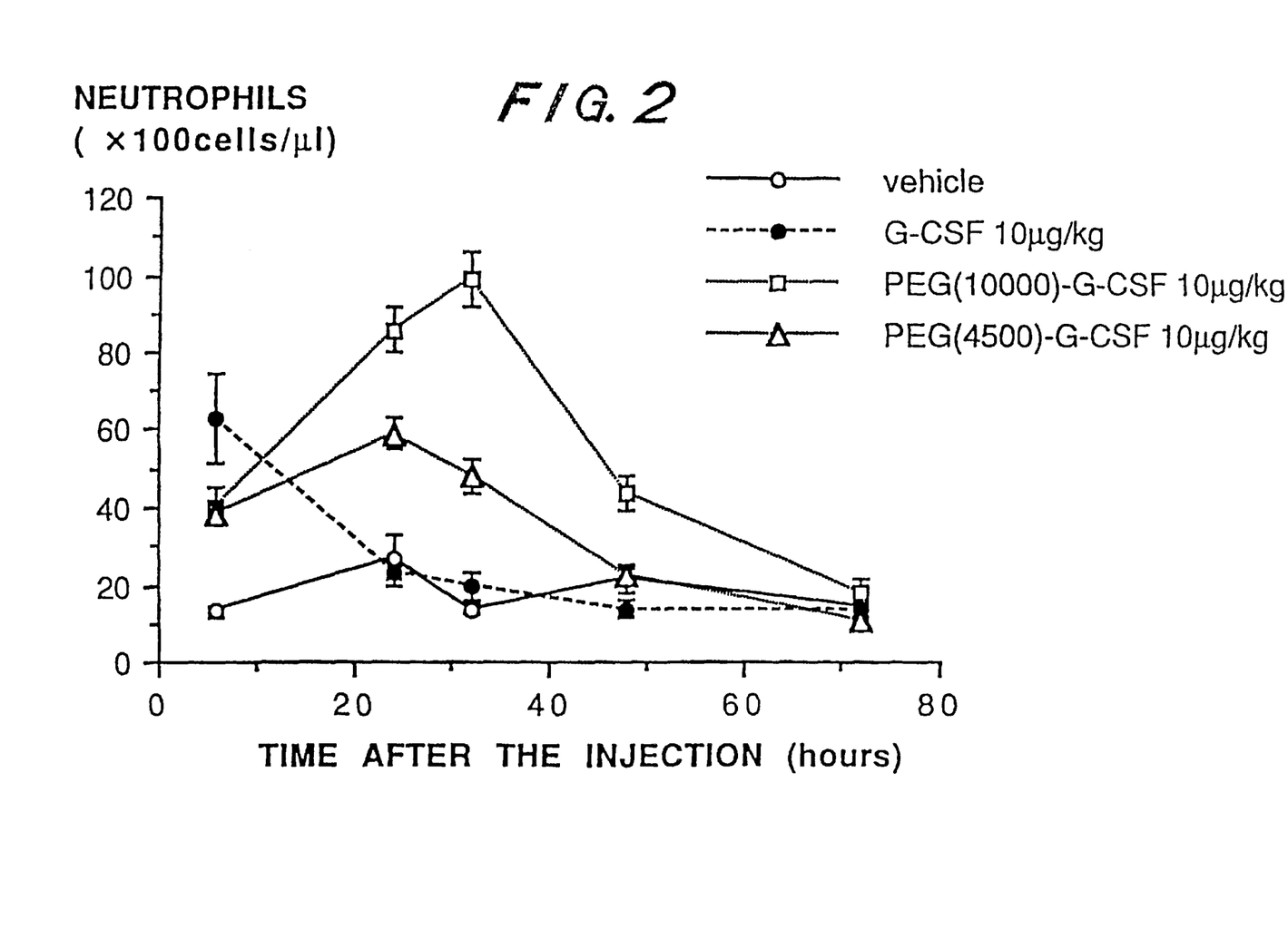
FIG. 2 shows the time course of the change in number of neutrophils in mice after administration with human G-CSF or PEG-modified G-CSF. Each point represents an average value obtained from six mice with a standard deviation.

As shown in FIG. 2, in the case of the intact human G-CSF, the number of neutrophils decreases to a basal level 24 hrs after the injection. On the other hand, a significant increase of neutrophils was observed over 32 hrs and 48 hrs after the injection for PEG (4,500) G-CSF and PEG (10,000) G-CSF, respectively.

Moreover, male ICR mice (8 weeks old) were intravenously administered with the PEG (10,000) G-CSFs obtained in EXAMPLE 3; (a) an average molecular weight of 30K, (b) an average molecular weight of 51K; 40K:58%, 66K:42% at a dose of 10 μg protein/kg. At 24 hours after the injection the number of neutrophils was counted as in EXAMPLE 5. The results are shown in TABLE 4.

TABLE 4

Pharmacological activity (in vivo) of PEG (10,000) G-CSF

| Group | Number of Animals | Number of Neutrophils ($\times 10^2/\mu l$) | Ratio (to vehicle) |
|---|---|---|---|
| Vehicle | 5 | 7.4 ± 0.6 | 1.0 |
| G-CSF | 5 | 16.4 + 3.1 | 2.2 |
| PEG(10,000)G-CSF (a) | 5 | 68.9 + 10.5 | 9.3 |
| PEG(10,000)G-CSF (b) | 5 | 95.8 + 6.4 | 12.9 |

Both PEG (10,000) G-CSF (a) and (b) increased the number of neutrophils more than intact human G-CSF. Especially, PEG (10,000) G-CSF, with a higher extent of the modification, showed a more remarkable increase in the number of neutrophils, as was the case with PEG (4,500) G-CSF.

EXAMPLE 8

Figure 3:
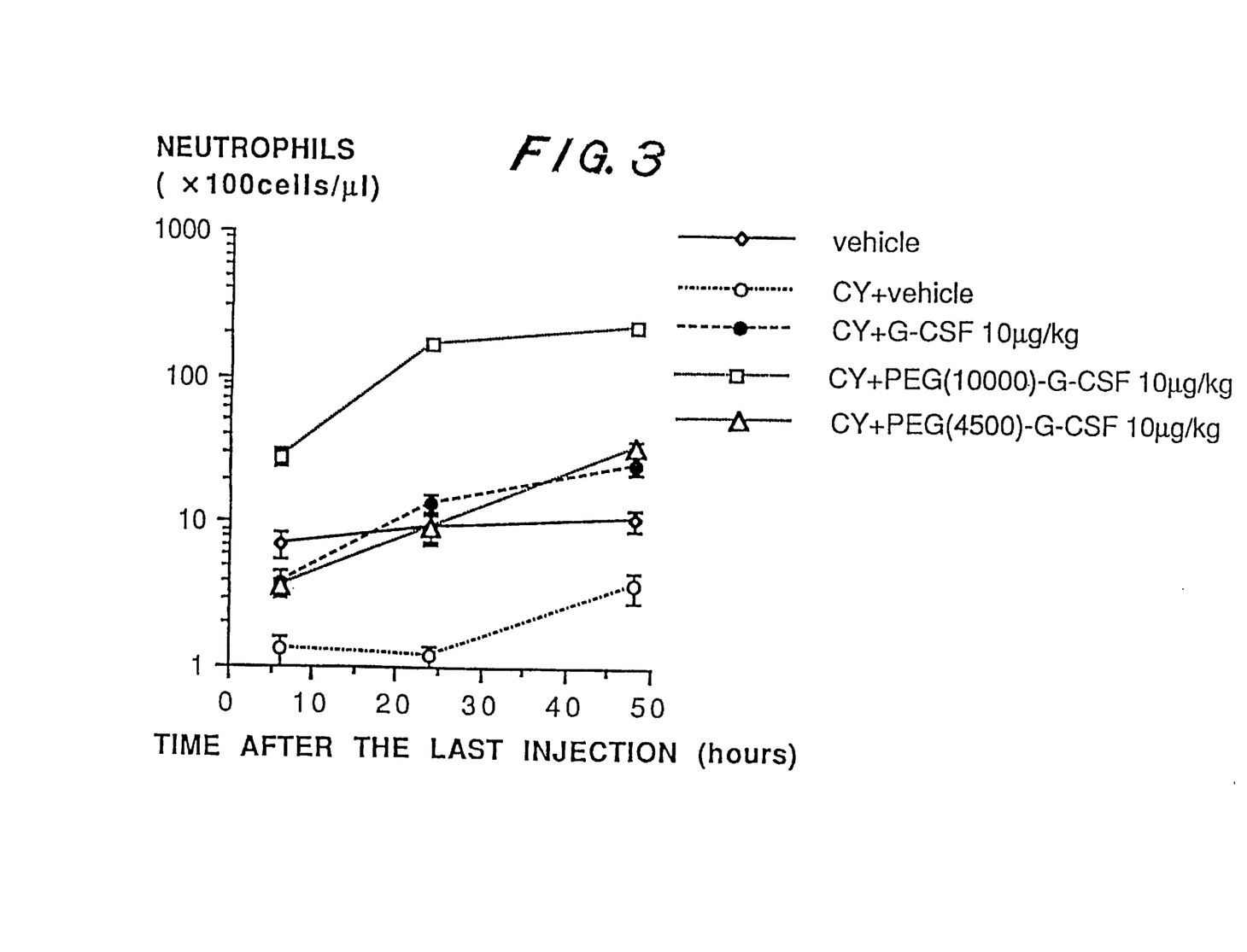
FIG. 3 shows an accelerating effect of PEG-modified human G-CSF on the recovery from neutropenia induced by cyclophosphamide. Each point represents an average value obtained from six mice with a standard deviation.

Effects of PEG-Modified Human G-CSF on Cyclophosphamide-Induced Neutropenic Mice le;.5qMale ICR mice (7 weeks old) were intraperitoneally injected with 200 mg/kg cyclophosphamide (CY) to induce neutropenia. Once a day for 4 successive days starting from one day after the CY injection, PEG (4,500) G-CSF and PEG (10,000) G-CSF as used in EXAMPLE 7 were intravenously injected into the neutropenic mice at a dose of 10 μg protein/kg. At 6, 24 and 48 hrs after the last injection, blood was collected from the orbital vein and neutrophils were counted as in EXAMPLE 5.

le;.5qAs shown in FIG. 3, PEG-modified G-CSFs accelerated the recovery from neutropenia induced by the injection of cyclophosphamide as early or earlier than the intact G-CSF. Especially, PEG (10,000) G-CSF effected a significant increase in the number of neutrophils.

EXAMPLE 9

Figure 4:
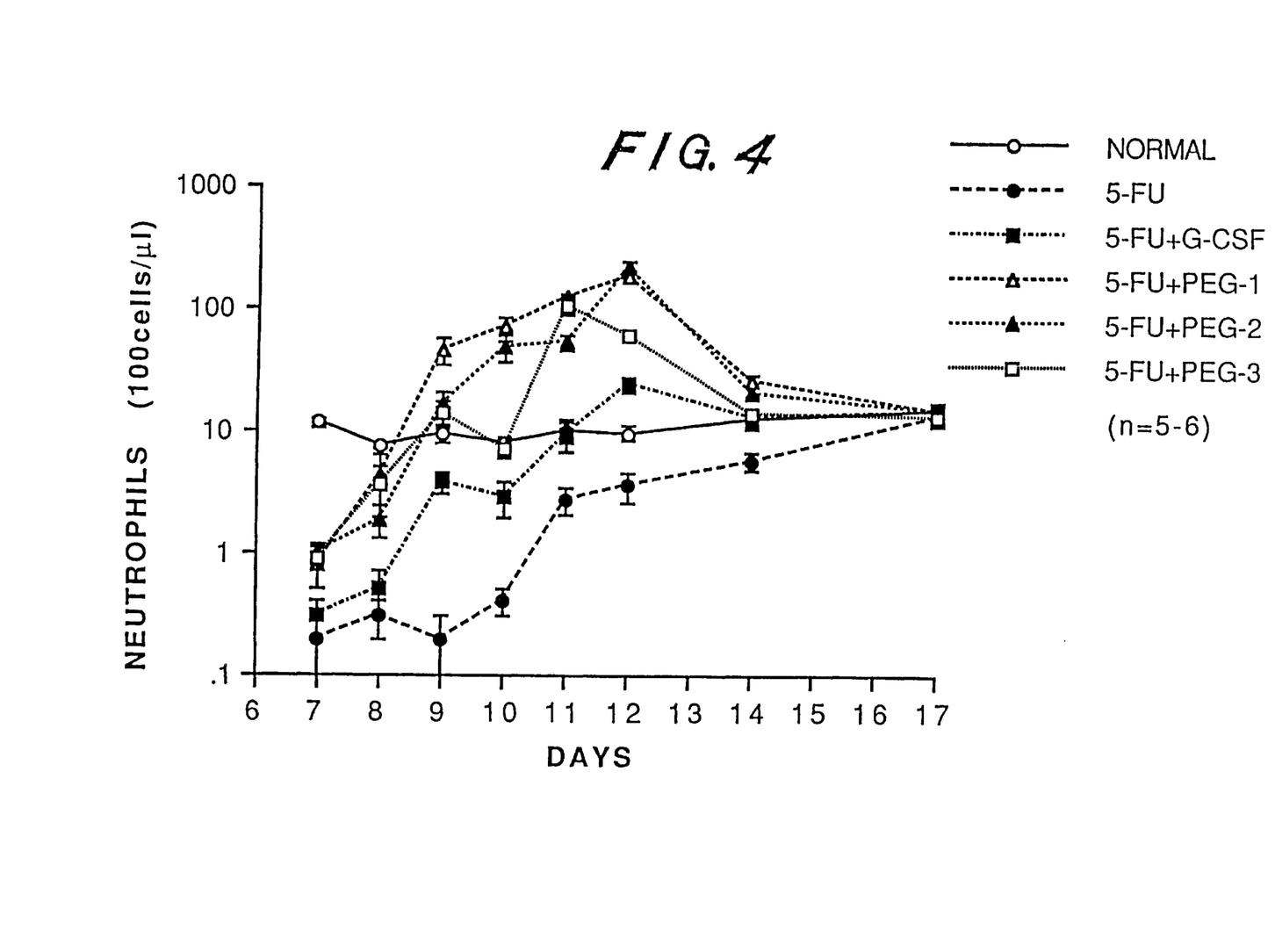
FIG. 4 shows an accelerating effect of PEG-modified G-CSF on the recovery from neutropenia induced by 5-FU. Each point represents an average value obtained from six mice with a standard deviation.

Effects of PEG-Modified Human G-CSF on 5-FU-Induced Neutropenic Mice le;.5qFemale $BDF_1$ mice (7 weeks old, JAPAN SLC Co.,) were intravenously injected with 200 mg/kg 5-FU to induce neutropenia. At a dose of 10 μg protein/kg either once a day for 11 successive days (PEG-1), or every other day (at day 1, 3, 5, 7, 9 and 11; PEG-2) and every third day (at day 1, 4, 7 and 10; PEG-3) starting from one day after the 5-FU injection, the same PEG (10,000) G-CSF as used in EXAMPLE 7 the intact human G-CSF were subcutaneously injected into the neutropenic mice. At day 7, 8, 9, 10, 11, 12, 14 and 17, blood was collected from orbital vein and neutrophils were counted as in EXAMPLE 5.

le;.5qAs shown in FIG. 4, it took about 14 days for recovery of neutrophil counts of mice injected with only 5-FU to a basal level. On the other hand, it took about 11 days and 9 days for recovery of neutrophil counts of mice injected also with the intact human G-CSF, and PEG-1, 2 and 3, respectively. Thus, PEG-modified G-CSFs accelerated recovery from neutropenia induced by the injection of 5-FU earlier than intact G-CSF. Moreover, even with fewer injections of the PEG-modified G-CSFs than the intact human G-CSF, the same phenomena as the above could be observed.

EXAMPLE 10

Acute Toxicity of PEG-Modified Human G-CSF le;.5qMale and female Slc:IR mice (5 weeks old) in groups consisting 6 mice each were intravenously administered with the same PEG (4,500) G-CSF or PEG (10,000) G-CSF as used in EXAMPLE 7 at a dose of 10 μg protein/kg, or with vehicle at a dose of 12 ml/kg. General conditions and survival of the treated mice were observed as often as possible for 6 hrs immediately after administration and once a day for the following 14 days. The body weight was checked at the day of injection, 5, 8, 12 and 15th days. Surviving mice were bled to death under ether anesthesia and subjected to pathologic autopsy.

As shown in TABLE 5, no mouse died for the observed period. LD 50 for both PEG (4,500) G-CSF and PEG (10,000) G-CSF was estimated over 3,000 μg protein/kg in both male and female mice. No remarkable change in general condition, body weight or opinion of the autopsy was observed for PEG (4,500) G-CSF or PEG (10,000) G-CSF. These results may suggest that the acute toxicity of PEG-modified human G-CSF is very weak, as the intact human G-CSF is

TABLE 5

Mortality of male and female mice

| Sex | Compound | Dose (μg/kg) | Number of deaths on day | | | | | | | | | | | | | | Mortality* | LD$_{50}$ (μg/kg) |
|---|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 (Day) | | |
| Male | Vehicle | — | 0 | 0 | 0 | 0 | 0 | 0 | 0 | 0 | 0 | 0 | 0 | 0 | 0 | 0 | 0 | 0/6 | — |
| | PEG4500-G-CSF | 3,000 | 0 | 0 | 0 | 0 | 0 | 0 | 0 | 0 | 0 | 0 | 0 | 0 | 0 | 0 | 0 | 0/6 | >3,000 |
| | PEG10000-G-CSF | 3,000 | 0 | 0 | 0 | 0 | 0 | 0 | 0 | 0 | 0 | 0 | 0 | 0 | 0 | 0 | 0 | 0/6 | >3,000 |
| Female | Vehicle | — | 0 | 0 | 0 | 0 | 0 | 0 | 0 | 0 | 0 | 0 | 0 | 0 | 0 | 0 | 0 | 0/6 | — |
| | PEG4500-G-CSF | 3,000 | 0 | 0 | 0 | 0 | 0 | 0 | 0 | 0 | 0 | 0 | 0 | 0 | 0 | 0 | 0 | 0/6 | >3,000 |
| | PEG10000-G-CSF | 3,000 | 0 | 0 | 0 | 0 | 0 | 0 | 0 | 0 | 0 | 0 | 0 | 0 | 0 | 0 | 0 | 0/6 | >3,000 |

*No. of dead animals/No. of treated animals

EXAMPLE 11

Determination of Half-Life of PEG-Modified hG-CSF

Figure 5:
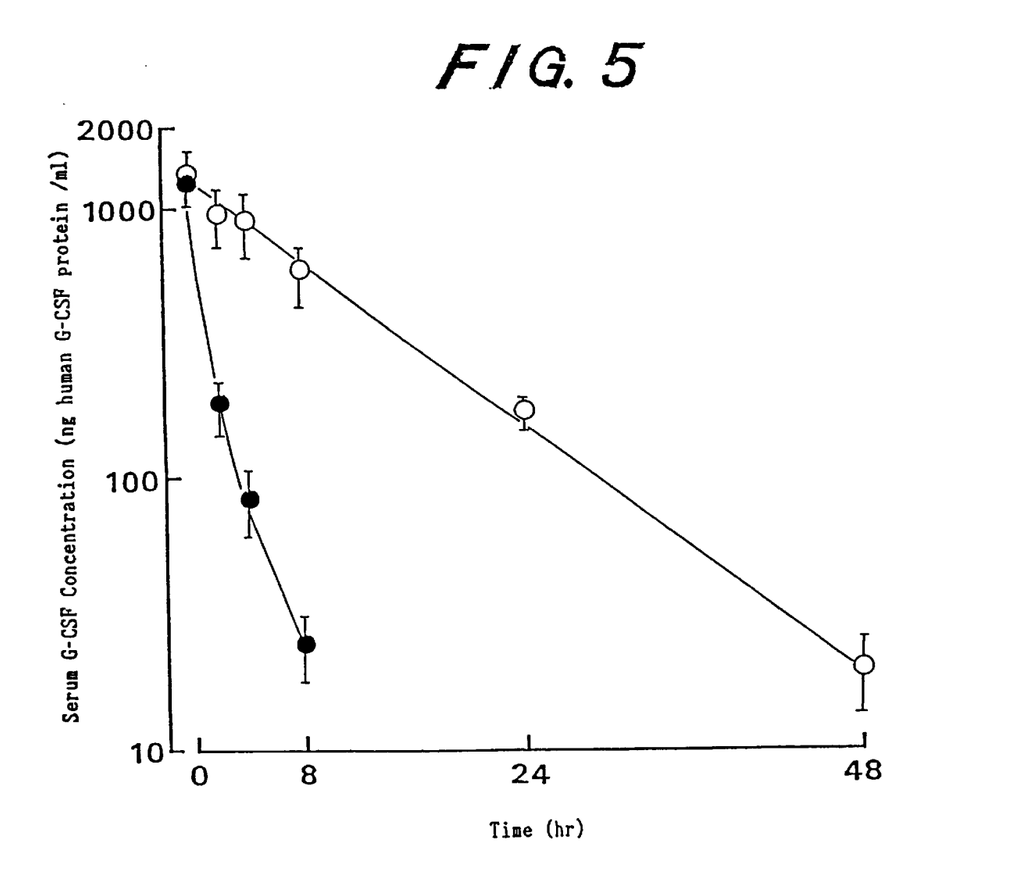
FIG. 5 shows the results obtained in the study of half-life in serum of PEG (10,000) G-CSF (○) and human G-CSF (●). Each point represents an average value from three rats with a standard deviation.

Male Sprague-Dawley rats (7 weeks old) were used for study of pharmacokinetics of the intact human G-CSF and PEG (10,000) G-CSF prepared in EXAMPLE 3. Samples were intravenously injected into rats at a dose of 100 μg protein/kg. At 10 min, 2, 4, 8, 24 and 48 hrs after the injection, about 6–7 ml of blood from each of three rats was collected from the abdominal aorta into a polypropylene tube of about 15 ml volume and centrifuged (18,000×g) at 4° C. for 5 min to prepare a serum fraction. The amount of the active human G-CSFs contained in the serum fraction was determined by a bioassay for proliferation induction of mouse bone marrow cells on the basis of incorporation of $^3$H-thymidine (Ralph et al., Blood 66, pp.633–639, (1988)). The time course of serum concentration is shown in FIG. 5. The results indicate that the half lives of the intact human G-CSF and PEG (10,000) G-CSF are 1.79 hrs and 7.05 hrs, respectively, and AUCs are also 2,000 ng protein hrs/ml and 16,195 ng protein hrs/ ml, respectively. Accordingly, it is demonstrated that the clearance rate of PEG (10,000) G-CSF in the body is less than that of the intact human G-CSF has.

Industrial Applicability le;.5qIt is expected that the present PEG-modified human G-CSF may make a great contribution to the treatment with human G-CSF because it has a much longer lasting neutrophil-increasing activity than that of the intact human G-CSF, enabling fewer numbers of administration with a lower dose.

We claim:

le;.5q1. A biologically active G-CSF polypeptide having at least one polyethylene glycol molecule covalently attached to at least one amino acid of the polypeptide, wherein said polyethylene glycol molecule is covalently attached through a carboxyl group of an amino acid of the polypeptide.

le;.5q2. A biologically active G-CSF polypeptide having at least one polyethylene glycol molecule covalently attached to at least one amino acid of the polypeptide, wherein the amino acid sequence of said G-CSF polypeptide is:

(Met)n

Thr Pro Leu Gly Pro Ala Ser Ser Leu Pro Gln

Ser Phe Leu Leu Lys Cys Leu Glu Gln Val Arg

Lys Ile Gln Gly Asp Gly Ala Ala Leu Gln Glu

Lys Leu Cys Ala Thr Tyr Lys Leu Cys His Pro

Glu Glu Leu Val Leu Leu Gly His Ser Leu Gly

Ile Pro Trp Ala Pro Leu Ser Ser Cys Pro Ser

Gln Ala Leu Gln Leu Ala Gly Cys Leu Ser Gln

Leu His Ser Gly Leu Phe Leu Tyr Gln Gly Leu

Leu Gln Ala Leu Glu Gly Ile Ser Pro Glu Leu

Gly Pro Thr Leu Asp Thr Leu Gln Leu Asp Val

Ala Asp Phe Ala Thr Thr Ile Trp Gln Gln Met

Glu Glu Leu Gly Met Ala Pro Ala Leu Gln Pro

Thr Gln Gly Ala Met Pro Ala Phe Ala Ser Ala

Phe Gln Arg Arg Ala Gly Gly Val Leu Val Ala

Ser His Leu Gln Ser Phe Leu Glu Val Ser Tyr

Arg Val Leu Arg His Leu Ala Gln Pro (n = 0 or 1)

* * * * *

UNITED STATES PATENT AND TRADEMARK OFFICE
CERTIFICATE OF CORRECTION

PATENT NO. : 5,824,778
DATED : October 20, 1998
INVENTOR(S) : Rika Ishikawa et al It is certified that error appears in the above-identified patent and that said Letters Patent is hereby corrected as shown below:

On the title page: Item [56]

Foreign Patent Document (12th patent listed) replace "62-36488 10/87 Japan" with --62-236488 10/87 Japan--.

Column 2, line 2, replace "present invention.." with --present invention.--.
Column 4, line 43, replace "an adult" with --an adult.--.
Column 4, line 52, replace "administration with" with --administration of--.
Column 5, lines 4-5, replace "not be" with --not to be-.
Column 6, line 21, replace "human G-SCF" with --human G-CSF--.
Column 7, line 9, replace "with distributed" with --which is distributed--.
Column 7, line 16, replace "(pH 10.0)" with --pH 10.0--.
Column 7, line 28, replace "with distributed" with --which is distributed--.
Column 9, line 61, in Table 4, replace "7.4 ± 0.6" with --7.4 + 0.6--.
Column 10, line 10, replace "Ie;5qMale ICR" with --Male ICR--.
Column 10, line 20, replace "Ie;5qAs shown" with --As shown--.

Signed and Sealed this

Nineteenth Day of December, 2000

Attest:

Q. TODD DICKINSON

*Attesting Officer*            Commissioner of Patents and Trademarks

UNITED STATES PATENT AND TRADEMARK OFFICE
CERTIFICATE OF CORRECTION

PATENT NO. : 5,824,778
DATED : October 20, 1998
INVENTOR(S) : Rika Ishikawa et al Page 2 of 2

It is certified that error appears in the above-identified patent and that said Letters Patent is hereby corrected as shown below:

Column 10, line 30, replace "le;5qFemale BDF$_1$," with --Female BDF$_1$--.
Column 10, line 34, replace "and every third" with --or every third--.
Column 10, line 39, replace "from orbital" with --from the orbital--.
Column 10, line 41, replace "le;5qAs shown" with --As shown--.
Column 10, line 57, replace "le;5qMale and female" with --Male and female--.
Column 10, line 61, replace "vehicle at" with --vehicle alone at--.
Column 11, line 9, replace "G-CSF is" with --G-CSF is.--.
Column 11, line 52, replace "human G-CSF has." with --human G-CSF.--.
Column 11, line 57, replace "le;5qIt is expected" with --It is expected--.
Column 11, line 65, replace "le;5q1. A biologically" with --1. A biologically--.
Column 12, line 4, replace le;5q2. A biologically" with --1. A biologically--.

Signed and Sealed this

Nineteenth Day of December, 2000

Attest:

Q. TODD DICKINSON

*Attesting Officer*  *Commissioner of Patents and Trademarks*